United States Patent [19] [11] 4,018,766
Brown et al. [45] Apr. 19, 1977

[54] SUBSTITUTED BENZOPYRANO[3,4-C]PYRIDINE-5-ONES

[75] Inventors: Richard E. Brown, East Hanover; Chester Puchalski, Dover; John Shavel, Jr., Mendham, all of N.J.

[73] Assignee: Warner-Lambert Company, Morris Plains, N.J.

[22] Filed: June 25, 1975

[21] Appl. No.: 590,346

Related U.S. Application Data

[63] Continuation-in-part of Ser. No. 534,502, Dec. 19, 1974, Pat. No. 3,946,008, which is a continuation-in-part of Ser. No. 343,613, March 21, 1973, abandoned, which is a continuation-in-part of Ser. No. 122,498, March 9, 1971, abandoned.

[52] U.S. Cl. .................... 260/247.2 B; 424/246; 424/248.55; 424/250; 424/263; 260/243 B; 260/268 TR; 260/293.58; 260/295 T

[51] Int. Cl.² ........................................ C07D 491/04
[58] Field of Search ................ 260/247.2 B, 295 T, 260/293.58, 268 TR, 243 B

[56] References Cited
UNITED STATES PATENTS 3,689,497 9/1972 Brown et al. ............... 260/295 T

*Primary Examiner*—Henry R. Jiles
*Assistant Examiner*—R. W. Ramsuer
*Attorney, Agent, or Firm*—Albert H. Graddis; Frank S. Chow; George M. Yahwak

[57] ABSTRACT

Disclosed are novel substituted benzopyranopyridines which are active as bronchodilators.

4 Claims, No Drawings

SUBSTITUTED BENZOPYRANO[3,4-C]PYRIDINE-5-ONES

This application is a continuation-in-part of our application Ser. No. 534,502, filed 19 Dec. 1974 now U.S. Pat. No. 3,946,008, the disclosure of which is hereby incorporated by reference, which in turn is a continuation-in-part of our application Ser. No. 343,613, filed 21 Mar. 1973 now abandoned, which in turn is a continuation-in-part of our application Ser. No. 122,498, filed 9 Mar. 1971, now abandoned.

This invention relates to novel substituted benzopyranopyridines of the formula I.

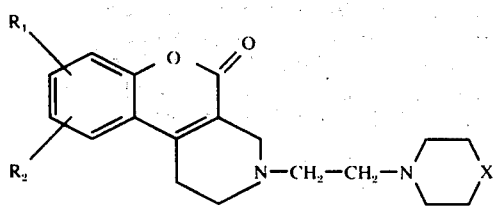

In the above formula, $R_1$ and $R_2$ may be hydrogen, hydroxy or lower alkyl of 1 to 6 carbon atoms with the proviso that either $R_1$ or $R_2$ must be lower alkyl and X may be oxygen, sulfur, $CH_2CH_2$, a bond connecting the adjacent carbon atoms or CH—$R_3$ or N—$R_3$ where $R_3$ may be hydrogen, a lower alkyl group of from 1 to 6 carbon atoms or a lower alkanoyl group of from 1 to 6 carbon atoms.

The compounds of this invention may be prepared in the same way as was described in detail in out U.S. Pat. No. 3,946,008 and consists of a condensation reaction between an appropriately substituted phenol of formula II and 3-carbethoxy-4-piperidone to give an $R_1$, $R_2$ substituted compound of formula III, which is subsequently alkylated with a halide of formula IV to give the subject compounds of formula I.

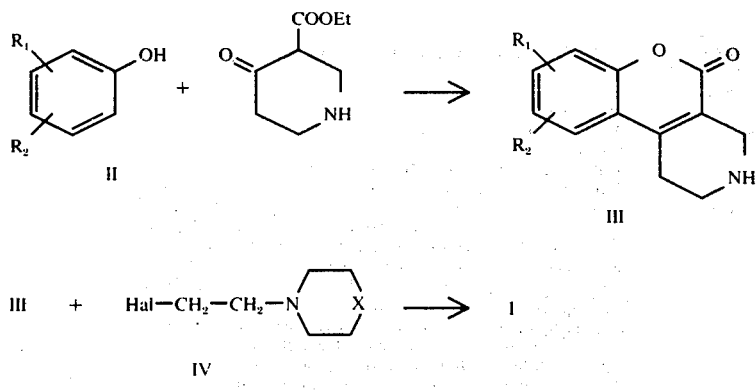

In the above formulae, $R_1$, $R_2$ and X are as described for I. Hal in structure IV refers to a halogen atom such as chlorine or bromine. The starting phenols of structure II are known compounds and are commercially available or are prepared by methods standard to the art.

The following examples are given in order to further illustrate the invention.

EXAMPLE 1

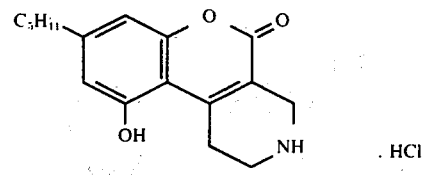

1,2,3,4-Tetrahydro-10-hydroxy-8-pentyl-5H-[1]benzopyrano[3,4-c]pyridin-5-one HCl. 150cc of cold $H_2SO_4$ was stirred and treated with 42.4g (0.234m) of olivetol portionwise, in 15 min., followed by addition of 48.6g (0.235m) of 3-carbethyoxy-4-piperidone HCl portionwise, in 15 min. After solution, the reaction was allowed to stand at room temperature for 8 days. The reaction was then cooled and poured onto 200g of ice. The resulting gum was isolated and particulated by trituration with two 250ml portions of $CH_3CN$. The resulting solid was suspended in 200ml of water and stirred for 2 hours maintaining a pH of 7–8 by periodic additions of conc. $NH_4OH$. After filtration 32g of solid was had. Crystallization from MeOH/HCl (gas) afforded analytical salt, m.p. 275°–80° C.

Anal. Calcd. for $C_{17}H_{21}NO_3$ HCl: C, 63.06; H, 6.85; N, 4.33; Cl, 10.95. Found: C, 62.79; H, 6.94; N, 4.29; Cl, 10.88.

EXAMPLE 2

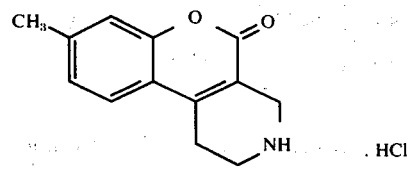

1,2,3,4-Tetrahydro-8-methyl-5H-[1]benzopyrano[3,4-c]pyridine-5-one hydrocloride. In the same way as described for example 1, 8.7g of m-cresol and 8.3g of 3-carbethoxy-4-piperidone were reacted to give after crystallization from 3N HCl, a crystalline hydrochloride salt, m.p. 281°–5° C.

Anal. Calcd. for $C_{13}H_{13}NO_2$. HCl: C, 62.03; H, 5.61; N, 5.56; Cl, 14.08. Found: C, 62.32; H, 5.58; N, 5.32; Cl, 14.04.

EXAMPLE 3

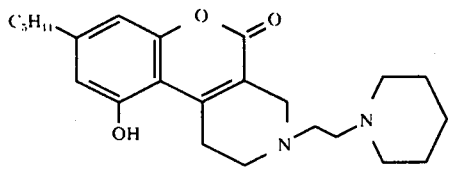

. 2HCl 1,2,3,4-Tetrahydro-10-hydroxy-8-pentyl-3-[2-(1-piperidinyl)ethyl]-5H-[1]benzopyrano[3,4-c]pyridin-5-one dihydrochloride. A mixture of 5.74g (0.02m) of 1,2,3,4-tetrahydro-10-hydroxy-8-pentyl-5H-[1]benzopyrano [3,4-c]pyridin-5-one HCl, 4.42g (0.024m) of N-chloroethylpiperidine HCl, and 4.85g (0.048m) of triethylamine in 200ml of ethanol was refluxed for 16 hours, filtered while hot and treated immediately with excess HCl gas. On cooling to room temperature, there was obtained 7.0g (75%) of crude dihydrochloride. Crystallization from methanol afforded analytical material, m.p. 256°–8° C.

Anal. Calcd. for $C_{24}H_{34}N_2O_3 \cdot 2HCl$: C, 61.18; H, 7.70; N, 5.95; Cl, 15.05. Found: C, 60.88; H, 7.66; N, 5.82; Cl, 14.94.

EXAMPLE 4

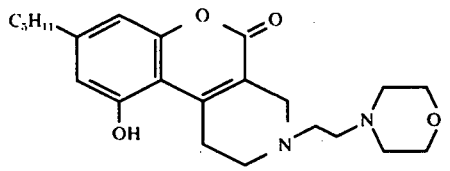

. 2HCl 1,2,3,4-Tetrahydro-10-hydroxy-3-[2-(4-morpholinyl)ethyl]-8-pentyl-5H-[1]benzopyrano[3,4-c]pyridin-5-one dihydrochloride. In a manner similar to example 3, 5.74g (0.02m) of 1,2,3,4-tetrahydro-10-hydroxy-8-pentyl-5H-[1]benzopyrano[3,4-c]pyridin-5-one hydrochloride, 4.45g (0.024m) of N-chloroethylmorpholine HCl, and 4.85g (0.048m) of triethylamine afforded 6.4g of product. Crystallization from MeOH gave analytical material, m.p. 232°–5° C.

Anal. Calcd. for $C_{23}H_{32}N_2O_4 \cdot 2HCl$: C, 58.35; H, 7.24; N, 5.92; Cl, 14.98. Found: C, 58.23; H, 7.37; N, 5.89; Cl, 14.72.

EXAMPLE 5

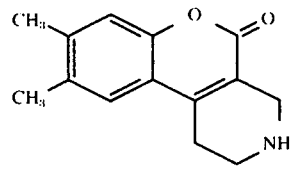

1,2,3,4-Tetrahydro-8,9-dimethyl-5H-[1]benzopyrano[3,4-c]pyridin-5-one. In the same way as described for example 1, 0.3m of 3,4-dimethyl phenol, 0.2m of 3-carbethoxy-4piperidone were reacted to give 8.4g of crude product. Crystallization from ethyl acetate afforded analytical material, m.p. 173°–5° C.

Anal. Calcd. for $C_{14}H_{15}NO_2$: C, 73.34; H, 6,59; N, 6.11. Found: C, 73.31; H, 6.50; N, 5.59.

EXAMPLE 6

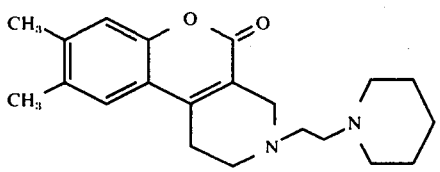

1,2,3,4-Tetrahydro-8,9-dimethyl-3[2-(piperidino)-ethyl]-5H-[1]benzopyrano[3,4-c]pyridine-5-one. In the same way as described in example 3, 4.2g of 1,2,3,4-tetrahydro-8,9-dimethyl-5H-[1]benzopyrano[3,4-c]pyridin-5-one, 4.05g of N-chloroethylpiperidine hydrochloride and 4.4g of triethylamine gave 5.0g of crude base. Crystallization from actronitrile gave analytical material, m.p. 142°–5° C.

Anal. Calcd. for $C_{21}H_{28}N_2O_2$: C, 74.08; H, 8.29; N, 8.23. Found: C, 73.99; H, 8.41; N, 8.26.

EXAMPLE 7

| TEST ANIMAL: | Male albino guinea pigs (250–350 gm) | |
|---|---|---|
| ROUTE OF ADMINISTRATION: | Intraperitoneal | |
| DOSES: | 25 mg/kg | |
| SPASMOGENS: | Acetylcholine chloride | 0.3% |
| | Histamine | 0.1% (most frequently used) |
| | Methacholine chloride (Mecholyl) | 0.1% |
| | Serotonin creatinine sulfate | 1.25% |
| PROCEDURE: | Pigs are continuously exposed to a spasmogen for 10 min.; delivery is by means of two nebulizers (Each nebulizer dispenses 0.2 cc/min.) positioned at the back of a closed, six unit plexiglas chamber (19 × 12½ × 9 in.) and driven by an air pressure of 10 lbs./in². The time from onset of the aerosol treatment to collapse of each animal is recorded; mean values for drug treated animals are compared to those of animals treated with vehicle. Guinea pigs that do not collapse during the 10 min. period are removed from the chamber and a maximum score of 10 is recorded. Test compounds (25 mg/kg, i.p.) are given 15 min. before exposure to spasmogen. | |

(See Siegmund, O.H. et al: J. Pharmacol and Exptl. Therapeutics, 90:254, 1949)

Following the protocol of Example 7, a series of tests were performed in which the compounds of the examples were compared to animals receiving only the spasmogen, histamine. The results obtained are given in the following table:

TABLE I

| Dose | No. Animals | Collapse Time |
| --- | --- | --- |
| Control | 3 | 2.3 |
| 25 mg. (Example 2) | 3 | 3.9 |
| Control | 3 | 1.9 |
| 25 mg (Example 3) | 3 | 10.0 |
| Control | 3 | 2.3 |
| 25 mg (Example 6) | 3 | 7.5 |

In each instance, and under identical test situations, the compounds of the present invention showed an ability to protect the animals from bronchial spasms.

The compounds of this invention are active as a bronchodilator for all spasmogens listed in Example 8, and protects the guinea pig against bronchospasm for a duration up to 4 hours at an oral dose of 10 mg/kg. Thus, it is more effective against bronchospasm than aminophylline, a commercial product used in the treatment of bronchial asthma and pulmonary edema, which protects the guinea pig against identical bronchospasm for less than two hours at a dose of 100 mg/kg. In addition, the compounds disclosed in this invention reverse pilocarpine or histamine bronchconstriction in the dog for a duration of up to 1 hour at an oral dose of 10 mg/kg. The bronochodilator activity exhibited by the N-substituted benzopyrano[3,4-c]pyridines described in this invention is the result of a direct smooth muscle relaxant effect on the bronchial tree as shown by in vitro experiments on guinea pig trachea. In these experiments, the N-substituted benzopyrano[3,4-c]pyridines are approximately 75 times more active than aminophylline in relaxing tracheal smooth muscle.

The compounds of this invention are useful for the treatment of bronchial asthma. Generally speaking, a dose of about 500 mg to 1000 mg several times daily is recommended for mammals weighing about 70 kilograms. The compounds can be administered orally or by parenteral administration.

In order to use these compounds they are formulated with pharmaceutically acceptable excipients such as lactose, starch, powdered sugar and the dosage forms can be tablets, capsules and the like. The dosage regimen can be varied according to the condition being treated by methods well known to the healing arts.

We claim:

1. A compound of the formula:

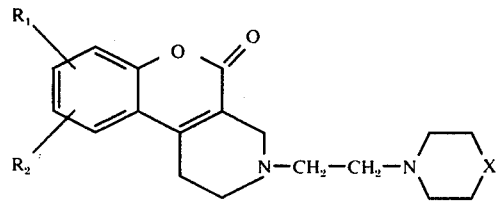

wherein $R_1$ and $R_2$ may be hydrogen, hydroxy, or lower alkyl of 1 to 6 carbon atoms, with the proviso that either $R_1$ or $R_2$ must be lower alkyl; and wherein X may be oxygen, sulfur, $-CH_2CH_2-$, a valence bond, $-CHR_3$ or $NR_3$ where $R_3$ is hydrogen, a lower alkyl of 1 to 6 carbon atoms, or a lower alkanoyl group of 1 to 6 carbon atoms.

2. The compound according to claim 1 wherein $R_1$ is $-C_5H_{11}$; $R_2$ is $-OH$; and X is $-CH_2-$, and which is 1,2,3,4-Tetrahydro-10-hydroxy-8-pentyl-3-[2-(1-piperidinyl)ethyl]-5H-[1]benzopyrano[3,4-c]pyridin-5-one dihychloride.

3. The compound according to claim 1 wherein $R_1$ is $-C_5H_{11}$; $R_2$ is $-OH$; and X is $-O-$, and which is 1,2,3,4-Tetrahydro-10-hydroxy-3-[2-(4-morpholinyl)ethyl]-8-pentyl-5H-[1]benzopyrano[3,4-c]pyridin-5-one dihydrochloride.

4. The compound according to claim 1 wherein $R_1$ and $R_2$ are $-CH_3$; and X is $-CH_2-$ and which is 1,2,3,4-Tetrahydro-8,9-dimethyl-3[2-(piperidino)-ethyl]-5H-[1]benzopyrano[3,4-c]pyridine-5-one.

* * * * *